(12) United States Patent
McDaniel et al.

(10) Patent No.: US 8,706,691 B2
(45) Date of Patent: Apr. 22, 2014

(54) SYSTEM FOR MANAGING INSULIN DOSAGE DATA

(75) Inventors: Angela S. McDaniel, Greensburg, IN (US); Ryan Scott McKinney, Brownsburg, IN (US); Morris J. Young, Noblesville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/556,434

(22) Filed: Jul. 24, 2012

(65) Prior Publication Data
US 2014/0032549 A1    Jan. 30, 2014

(51) Int. Cl.
    *G06F 7/00* (2006.01)
(52) U.S. Cl.
    USPC .......................................................... 707/621
(58) Field of Classification Search
    USPC .......................................................... 707/621
    See application file for complete search history.

(56) References Cited

U.S. PATENT DOCUMENTS

| 6,668,196 B1 | 12/2003 | Villegas et al. |
| 2002/0193679 A1 | 12/2002 | Malave et al. |
| 2011/0172635 A1* | 7/2011 | Estes .............................. 604/504 |

* cited by examiner

*Primary Examiner* — Truong Vo
(74) *Attorney, Agent, or Firm* — Harness, Dickey (57) ABSTRACT

A method is provided for managing insulin dosage data collected over a complete day and a partial day. The method includes providing, by an insulin pump, a plurality of insulin dosages over a complete day and a partial day and recording the insulin dosages. The method also includes recognizing a completion of the complete day, recording an end-of-day marker, and associating the end-of-day marker to the dosages delivered during the complete day. Moreover, the method includes identifying complete day dosage data and partial day dosage data. Additionally, the method includes performing a calculation of insulin dosage statistics and/or displaying and distinguishing between the complete day dosage data and the partial day dosage data. The calculation includes the complete day dosage data and excludes the partial day dosage data.

22 Claims, 4 Drawing Sheets

DELIVERED BOLUS DOSAGES

|   | A<br>Date | B<br>Time | C<br>Dosage(units) | D<br>Complete day? |
|---|---|---|---|---|
| 1 | 11/14/11 | 12:36PM | 6.60 | X |
| 2 | 11/14/11 | 3:59PM | 9.00 | X |
| 3 | 11/14/11 | 7:28PM | 25.00 | X |
| 4 | 11/15/11 | 9:29AM | 11.50 | X |
| 5 | 11/15/11 | 3:43PM | 5.00 | X |
| 6 | 11/15/11 | 6:14PM | 25.00 | X |
| 7 | 11/15/11 | 7:34PM | 17.00 | X |
| 8 | 11/16/11 | 9:35AM | 6.00 | X |
| 9 | 11/16/11 | 1:25PM | 11.00 | X |
| 10 | 11/16/11 | 3:57PM | 8.00 | X |
| 11 | 11/16/11 | 6:12PM | 25.00 | X |
| 12 | 11/16/11 | 6:43PM | 18.50 | X |
| 13 | 11/17/11 | 5:22AM | 3.10 | |
| 14 | 11/17/11 | 8:54AM | 9.60 | |
| 15 | 11/17/11 | 11:10AM | 16.30 | |
| 16 | 11/17/11 | 6:32PM | 7.10 | |
| 17 | 11/17/11 | 6:44PM | 17.00 | |
| 18 | 11/17/11 | 9:38PM | 6.00 | |

DELIVERED BASAL DOSAGES

|   | Date | Time Range | Flow Profile | Complete day? |
|---|---|---|---|---|
| 19 | 11/14/11 | 12:00AM - 7:09AM | 1 | X |
| 20 | 11/14/11 | 8:54AM - 11:58AM | 2 | X |
| 21 | 11/14/11 | 12:20PM - 8:40PM | 1 | X |
| 22 | 11/14/11 | 10:41PM - 11:59PM | 1 | X |
| 23 | 11/15/11 | 12:00AM - 11:59PM | 1 | X |
| 24 | 11/16/11 | 12:00AM - 7:15PM | 1 | X |
| 25 | 11/16/11 | 9:28PM - 11:59PM | 1 | X |
| 26 | 11/17/11 | 12:00AM - 6:32PM | 1 | |

SYSTEM FOR MANAGING INSULIN DOSAGE DATA

FIELD

The present disclosure relates to data management and, more particularly, relates to a system for managing insulin dosage data.

BACKGROUND

Diabetes mellitus, often referred to as diabetes, is a chronic condition in which a person has elevated blood glucose levels that result from defects in the body's ability to produce and/or use insulin. Diabetes can be treated by injecting predetermined dosages of insulin to the patient to control the level of glucose in the bloodstream. For instance, some diabetes patients rely on an insulin pump to deliver the predetermined dosages to the patient.

Patients can receive multiple types of insulin dosages, and the dosages can be delivered according to varying schedules. For instance, the insulin pump can deliver basal insulin dosages (i.e., insulin that is delivered continuously at an adjustable basal rate to deliver necessary insulin between meals and at night). The insulin pump can also deliver bolus dosages (i.e., insulin delivered at specific times before the patient eats and/or to correct a high blood glucose level). Moreover, the pump can be configured to deliver multiple types of bolus dosages (e.g., a "standard bolus," an "extended bolus," a "combination bolus/multiwave bolus," or other type. These dosages can be adjusted according to the patient's particular physiology, eating habits, etc.

Patients with diabetes and/or medical professionals sometimes record data relating to the insulin dosages that are delivered. This data can be used for identifying the effectiveness of the patient's particular insulin delivery schedule in maintaining the patient's blood glucose within a desirable range. The data can also be used for improving the patient's insulin delivery schedule, insulin delivery parameters such as time blocks and bolus advice parameters. Because there are many dosage amounts, dosage types, delivery times, etc., gathering and managing the data can be very difficult.

SUMMARY

This section provides a general summary of the disclosure, and is not a comprehensive disclosure of its full scope or all of its features.

A computer-implemented method for managing insulin dosage data collected over the course of multiple days to a person having diabetes is disclosed. The method includes providing, by an insulin pump, a plurality of insulin dosages over a time period. The time period includes a complete day and a partial day. The method also includes recording, by the insulin pump into a memory device, the plurality of insulin dosages. Additionally, the method includes recognizing, by the insulin pump, a completion of the complete day. Furthermore, the method includes recording, by the insulin pump into the memory device, an end-of-day marker as a result of recognizing the completion of the complete day. Moreover, the method includes associating, by the insulin pump, the end-of-day marker to those of the plurality of insulin dosages delivered during the complete day. Still further, the method includes identifying, by a data managing device, those of the plurality of insulin dosages associated with the end-of-day marker as complete day dosage data and identifying, by the data managing device, those of the plurality of insulin dosages unassociated with the end-of-day marker as partial day dosage data. The method can also include performing, by the data managing device, a calculation of insulin dosage statistics, wherein the calculation includes the complete day dosage data and the calculation excludes the partial day dosage data. Additionally, the method can include displaying, by the data managing device, both the complete day dosage data and the partial day dosage data to distinguish between the complete day dosage data and the partial day dosage data.

An insulin management system is also disclosed that manages insulin dosage data collected over the course of multiple days to a person having diabetes. The insulin management system includes an insulin pump with a memory device. The insulin pump is operable to provide a plurality of insulin dosages over a time period including a complete day and a partial day. The insulin pump is also operable to record the plurality of insulin dosages into the memory device. Moreover, the insulin pump is operable to recognize a completion of the complete day and record an end-of-day marker into the memory device as a result of the completion of the complete day. The insulin pump is further operable to associate the end-of-day marker to those of the plurality of insulin dosages delivered during the complete day. Furthermore, the insulin management system includes a data managing device that is operable to receive from the insulin pump the plurality of insulin dosages and the end-of-day marker associated with those of the plurality of insulin dosages delivered during the complete day. The data managing device is also operable to identify those of the plurality of insulin dosages associated with the end-of-day marker as complete day dosage data and to identify those of the plurality of insulin dosages unassociated with the end-of-day marker as partial day dosage data. The data managing device can also include a processor that is operable to perform a calculation of insulin dosage statistics. The calculation includes the complete day dosage data and excludes the partial day dosage data. Additionally, the data managing device can include a display that is operable to display both the complete day dosage data and the partial day dosage data to distinguish between the complete day dosage data and the partial day dosage data.

Furthermore, a computer-implemented method for managing insulin dosage data collected by an insulin pump over the course of multiple days to a person having diabetes is disclosed. The method includes receiving, by a data managing device from an insulin pump, a collection of data that reflects a plurality of insulin dosages delivered by the insulin pump over the course of a complete day and a partial day. The collection of data also includes an end-of-day marker that the insulin pump has associated with those of the plurality of insulin dosages delivered throughout the complete day. Also, the method includes identifying, by the data managing device, those of the plurality of insulin dosages associated with the end-of-day marker as complete day dosage data and identifying, by the data managing device, those of the plurality of insulin dosages unassociated with the end-of-day marker as partial day dosage data. Moreover, the method can include performing, by the data managing device, a calculation of insulin dosage statistics, wherein the calculation includes the complete day dosage data and excludes the partial day dosage data. Also, the method can include displaying, by the data managing device, both the complete day dosage data and the partial day dosage data to distinguish between the complete day dosage data and the partial day dosage data.

Still further, a computer-implemented method for managing insulin dosage data administered over the course of multiple days to a person having diabetes is disclosed. The method includes providing, by an insulin pump, a plurality of insulin dosages over a time period including a complete day and a partial day. The plurality of insulin dosages includes a plurality of basal insulin dosages and a plurality of bolus insulin dosages. Also, the method includes recording, by the insulin pump into a memory device, the plurality of insulin dosages. The method additionally includes recognizing, by the insulin pump, a completion of the complete day and recording, by the insulin pump into the memory device, an end-of-day marker as a result of recognizing the completion of the complete day. Furthermore, the method includes associating, by the insulin pump, the end-of-day marker to those of the plurality of insulin dosages delivered during the complete day. Additionally, the method includes transferring the plurality of insulin dosages and the end-of-day marker associated with those of the plurality of insulin dosages delivered during the complete day from the insulin pump to a data managing device. Moreover, the method includes identifying, by the data managing device, those of the plurality of insulin dosages associated with the end-of-day marker as complete day dosage data and identifying, by the data managing device, those of the plurality of insulin dosages unassociated with the end-of-day marker as partial day dosage data. Also, the method includes performing, by the data managing device, a calculation of insulin dosage statistics. The calculation includes the complete day dosage data, and the calculation excludes the partial day dosage data. Furthermore, the method includes displaying, by the data managing device, both the complete day dosage data and the partial day dosage data to distinguish between the complete day dosage data and the partial day dosage data.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figures 1, 4:
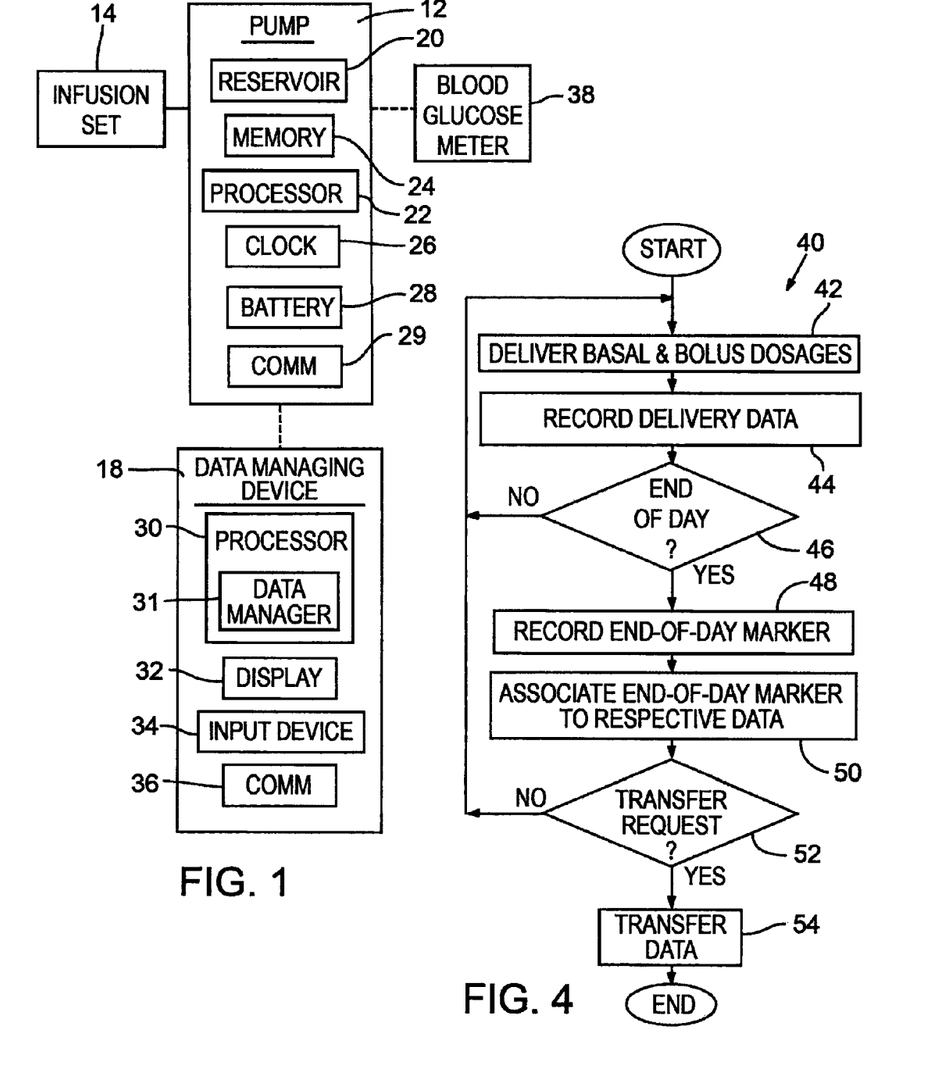
FIG. 1 is a schematic illustration of an insulin management system according to various exemplary embodiments of the present disclosure.
FIG. 4 is a flowchart representing exemplary methods of operating an insulin pump of the system illustrated in FIG. 1.

Referring initially to FIG. 1, an insulin management system 10 is illustrated schematically. The system 10 can generally include an insulin pump 12, an infusion set 14, and a data managing device 18.

The insulin pump 12 can incorporate various features of a known insulin pump 12. Thus, the insulin pump 12 can include at least one refillable reservoir 20, which contains insulin, and that selectively delivers insulin (e.g., via the selective mechanical action of a cartridge within the reservoir 20, etc.). The pump 12 can also include a processor 22 (i.e., controller). The processor can include programmed logic and other elements for controlling the amount of insulin delivered from the reservoir 20, the time that the insulin is delivered, the rate of delivery, etc. The pump 12 can additionally include a memory device 24, which can collect and store insulin dosage data as well as other data as will be discussed below. The memory device 24 can also include one or more predefined dosage schedules (i.e., dosage "profiles") that are tailored to the particular patient, and the processor 22 can access these profiles for controlling the amount of insulin delivered, the time of delivery, the rate of delivery, etc. Also, the pump 12 can include a clock 26, which keeps track of the current date and time. By monitoring the clock 26, the processor 22 can detect completion of a day (i.e., can detect an end-of-day event) for purposes that will be discussed below. For instance, if the current time reads 11:59 PM and 59 seconds on the clock 26, the processor 22 can determine that the end-of-day event has occurred. In additional embodiments, the clock 26 can automatically set a twenty-four hour timer at the beginning of every day (e.g., at 12:00 AM), and when the timer runs out or resets, the processor 22 can determine that the end-of-day event has occurred. The end-of-day event can be detected in other ways without departing from the scope of the present disclosure as well. Moreover, the pump 12 can include a power source, such as a battery 28, for providing power to the components of the pump 12. The battery 28 can include a main battery that supplies power for normal operations of the pump 12, and the battery 28 can include a backup battery that supplies power for only essential operations of the pump 12 when the main battery fails. It will be appreciated that the pump 12 can include additional or alternative power sources (e.g., one or more capacitors, etc.) without departing from the scope of the present disclosure.

Thus, the processor 22 can output control commands for causing predetermined amounts of insulin to be delivered at predetermined times and/or at predetermined flow rates. Also, as will be discussed in greater detail below, the insulin pump 12 can collect data relating to the amount of insulin delivered, the delivery time, the delivery rate, etc.

The pump 12 can further include a communications device 29. The communication device 29 can establish communications between the pump 12 and the data managing device 18 as will be discussed in detail below. Thus, data collected by the insulin pump 12 can be transmitted to the data managing device 18. The communications device 29 can include a wireless transmitter (e.g., BLUETOOTH™ transmitter, etc.), and/or the communications device 29 can include a connector for connecting a wire between the pump 12 and the data managing device 18. Also, the communications device 29 can transmit data to the data managing device 18 via the internet. It will be appreciated that the pump 12 can include additional or alternative communication devices and communication methods without departing from the scope of the present disclosure.

In additional embodiments, the insulin pump 12 can include an output device. For instance, in the embodiments illustrated, the insulin pump 12 includes a display 32, such as a computer monitor. Other types of output devices are within the scope of the present disclosure, however, such as a speaker, a printer, etc. The output device can output information of various types to the patient as will be discussed in greater detail below. The insulin pump 12 can further include an input device, such as buttons, dials, a touchscreen, etc. With the input device, the patient can input commands for controlling the pump 12.

Also, the infusion set 14 can be of a known type. Thus, the infusion set 14 can include a cannula that is inserted subcutaneously into the patient (i.e., the user, the person with diabetes, etc.). The infusion set 14 can be fluidly connected to the reservoir 20 of the pump 12. As such, insulin can be delivered from the reservoir 20 and into the patient's bloodstream via the infusion set 14.

Moreover, the data managing device 18 can be embodied on a computer (e.g., a desktop computer or portable computer such as a laptop, tablet, PDA, etc.). The data managing device 18 can include a processor 30 that implements various software, such as a data manager 31, for performing calculations and otherwise processing the data collected by the pump 12 as will be discussed in greater detail below. The data managing device 18 can further include a display 32 that can visually output the data that has been processed by the processor 30. Moreover, the data managing device 18 can include an input device 34, such as a keyboard, a touchscreen, etc., with which the user can input commands for controlling the data managing device 18. Also, the data managing device 18 can include a communication device 36 that can selectively communicate with the communications device 29 for receiving data collected by the pump 12. The communications device 36 of the data managing device 18 can communicate with the communications device 29 of the pump 12 wirelessly, via a hardwire connection, over the internet, etc.

In the embodiments represented in FIG. 1, the data managing device 18 is separate and distinct from the insulin pump 12. As such, data can be transmitted from the pump 12 to the data managing device 18, and the user can use the data managing device 18 separately from the pump 12 for analyzing and outputting the data. However, in some embodiments, the data managing device 18 can be included within the insulin pump 12 (e.g., embodied within the housing of the insulin pump 12) without departing from the scope of the present disclosure. In these latter embodiments, the pump 12 can include components, such as a computerized display, for implementing the data managing device 18 therein.

As shown in FIG. 1, the system 10 can further include a blood glucose meter 38. The blood glucose meter 38 can be of a known type. As such, the meter 38 can be used for detecting the current (i.e., actual) blood glucose level of the patient. More specifically, the patient can apply blood to a test strip (not shown), and the meter 38 can receive the strip and detect the amount of glucose in the blood thereon. In some embodiments, the meter 38 can be in operative communication with the pump 12, and the blood glucose level can be communicated to the pump 12 for controlling the amount of insulin (e.g., a bolus dosage of insulin) delivered to the patient. Although the blood glucose meter 38 is shown in FIG. 1 as being distinct from the data managing device 18, it will be appreciated that the blood glucose meter 38 and data managing device 18 could be combined into a single device within a single housing. Moreover, it will be appreciated that, in some embodiments, the blood glucose meter 38 or the data managing device 18 could be used for remotely controlling the pump 12 (e.g., to send control commands to the pump 12 to start and stop pumping, etc.).

Referring now to FIG. 4, exemplary embodiments of a method 40 of operating the insulin pump 12 will be discussed. As shown, the method 40 can begin in block 42, wherein basal insulin dosages and bolus insulin dosages are delivered to the patient. Then, in block 44, the insulin pump 12 can record the plurality of insulin dosages delivered in block 42 into the memory device 24.

More specifically, the memory device 24 of the insulin pump 12 can include one or more predetermined, programmed "delivery profiles" (i.e., schedules) for the automatic delivery of basal and/or bolus insulin dosages. These profiles can dictate the time of delivery, the amount of insulin to deliver, the rate that the insulin is delivered, etc. In block 42 of the method 40 of FIG. 4, the processor 22 can access the profile(s) stored in the memory device 24, and the processor 22 can send corresponding command signals to deliver the basal and/or bolus dosages from the reservoir 20 and into the patient's bloodstream via the infusion set 14 according to the profile(s). Also, in some embodiments, the user can manually input commands such that user-determined bolus dosages are delivered at desired times to reduce current blood glucose levels.

Then, in block 44, the processor 22 can record the actual basal and/or actual bolus insulin dosages delivered in block 42 of the method 40. For instance, the pump 12 can detect the amount of bolus insulin actually delivered and the corresponding time of delivery (i.e., the calendar date and the time of day). Also, the pump 12 can detect the amount of basal insulin actually delivered, the flow rate of the basal insulin, and the time of delivery (i.e., the range of time that the basal insulin is delivered). The processor 22 can obtain the time of delivery of these dosages from the clock 26. Then, the processor 22 can record this dosage data into the memory device 24.

Figure 2:
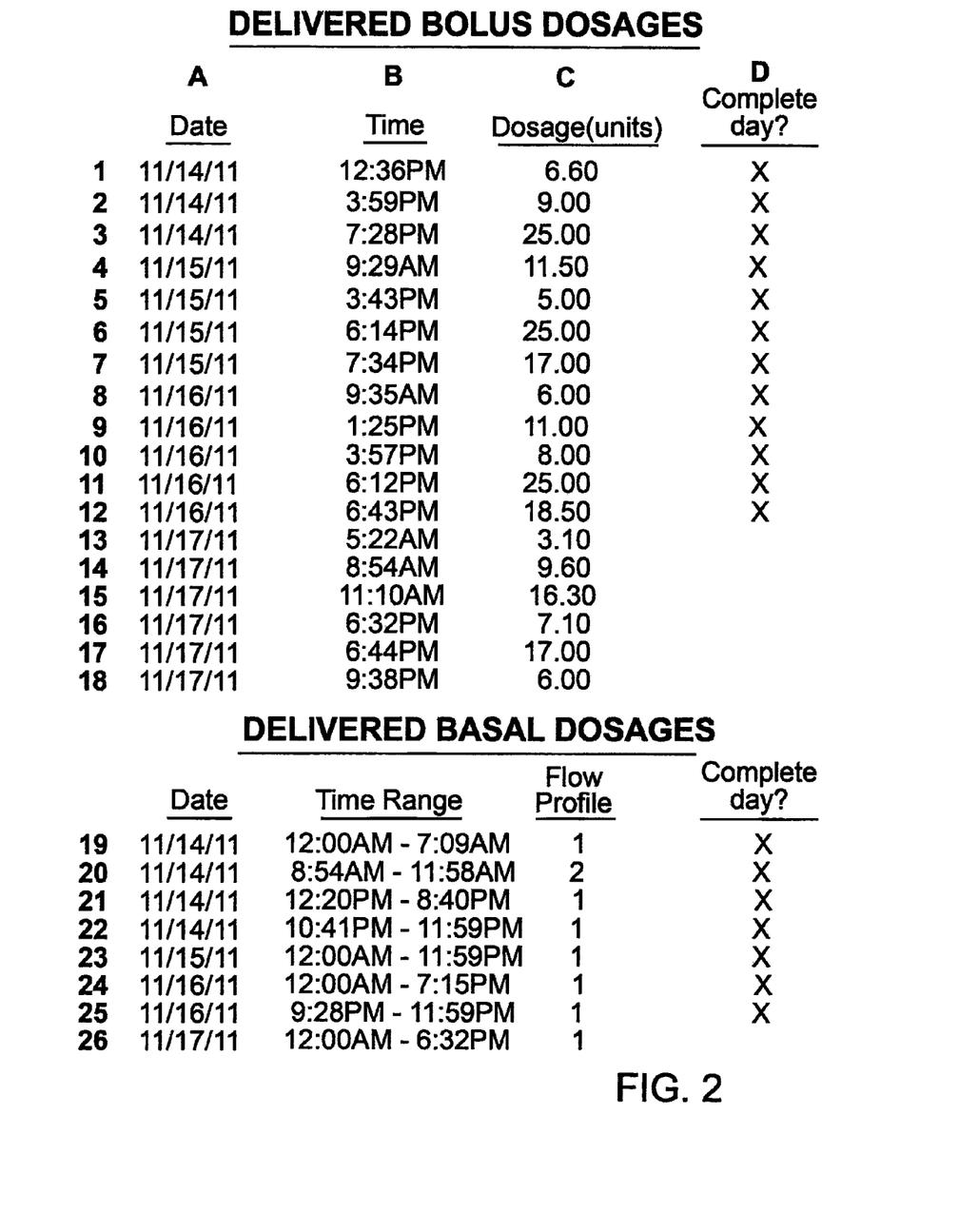
FIG. 2 is a table that includes exemplary insulin dosage data that is collected by an insulin pump of the system of FIG. 1.

FIG. 2 is an exemplary embodiment of the data collected in block 44. As shown, basal and bolus dosages are delivered over a time period from 12:00 AM on Nov. 14, 2011 and 9:38 PM on Nov. 17, 2011. The bolus dosages are individual events with predetermined insulin amounts (units) (column C, lines 1-18) delivered on specific dates (column A, lines 1-18) and at specific times (column B, lines 1-18). The basal dosages are those delivered at a predetermined rate (units/hour) that can vary over time according to a predetermined flow profile (column C, lines 19-26). In the embodiments illustrated, there is a "flow profile 1" and a "flow profile 2," each dictating a particular flow rate that can vary according to the date (column A, lines 19-26) and time (column B, lines 19-26). However, it will be appreciated that there can be any number of flow profiles.

In the embodiments shown in FIG. 2, dosage data is collected over a time period including three complete days (i.e., November 14, 15, and 16) and a partial day (i.e., November 17). For purposes of discussion, the data for November 14, 15, and 16 will be considered "complete day dosage data," and data for November 17 will be considered "partial day dosage data."

Next, in block 46 of FIG. 4, the pump 12 can determine whether it is the end of the particular day (i.e., recognize completion of a day or an end-of-day event). As mentioned, the processor 22 can recognize an end-of-day event when the clock reads 11:59 PM and 59 seconds at the end of each day of operation; however, the end-of-day event can be detected using an automatically resetting twenty-four hour timer or in any other way without departing from the scope of the present disclosure.

If the current time is prior to the end of the current day (i.e., block 46 answered negatively), then blocks 42 and 44 can be repeated. Thus, bolus and basal insulin dosages, delivery times, flow rates, etc. can be continuously recorded over the course of each day.

However, once the particular day has ended (i.e., block 46 answered positively), then block 48 can follow, and an end-of-day marker can be recorded. Then, in block 50, the end-of-day marker can be associated with that day's dosage data. More specifically, the processor 22 can monitor the clock 26 and as soon as the clock 26 indicates completion of the particular day (e.g., the clock 26 reads 11:59 PM and 59 seconds), the processor 22 can determine that the end of the day has been reached, and block 46 can be answered affirmatively. As a result, the processor 22 can record and associate an end-of-day marker with the respective insulin dosage data in the memory device. The end-of-day markers for the data shown in FIG. 2 are represented by an "X" in column D.

In the example of FIG. 2, since data was obtained over the course of the entire days of November 14, 15, and 16, there is an end-of-day marker for the insulin dosage data for those days. However, since the data was obtained over part of the day of November 17, there is no end-of-day marker for that insulin dosage data.

Subsequently, in block 52 of the method 40 of FIG. 4, the pump 12 determines whether a data transfer request has been received from the data managing device 18. If not (i.e., block 52 answered negatively), then the method 40 can loop back to block 42. However, if the data managing device 18 does request that the insulin dosage data be transferred (i.e., block 52 answered positively), then block 54 follows, and the insulin dosage data represented in FIG. 2 is transferred from the memory device 24 of the pump 12 to the data managing device 18. The data can be transferred via the communication devices 29, 36 of the pump 12 and data managing device 18, respectively.

It will be appreciated that the data transfer request of block 52 can be received in various ways. For instance, in some embodiments, the data transfer request might only be received by the pump 12 when the pump 12 is selectively placed in a so-called "communication mode" (i.e., communication with the data managing device 18 is enabled), such that the pump 12 is able to receive the data transfer request from the data managing device 18. Also, in some embodiments, the pump 12 can request to communicate with the data managing device 18 before the pump 12 receives the data transfer request from the device 18. Moreover, it will be appreciated that the pump 12 can continue to pump insulin when communicating and transferring data to the data managing device 18.

Figure 5:
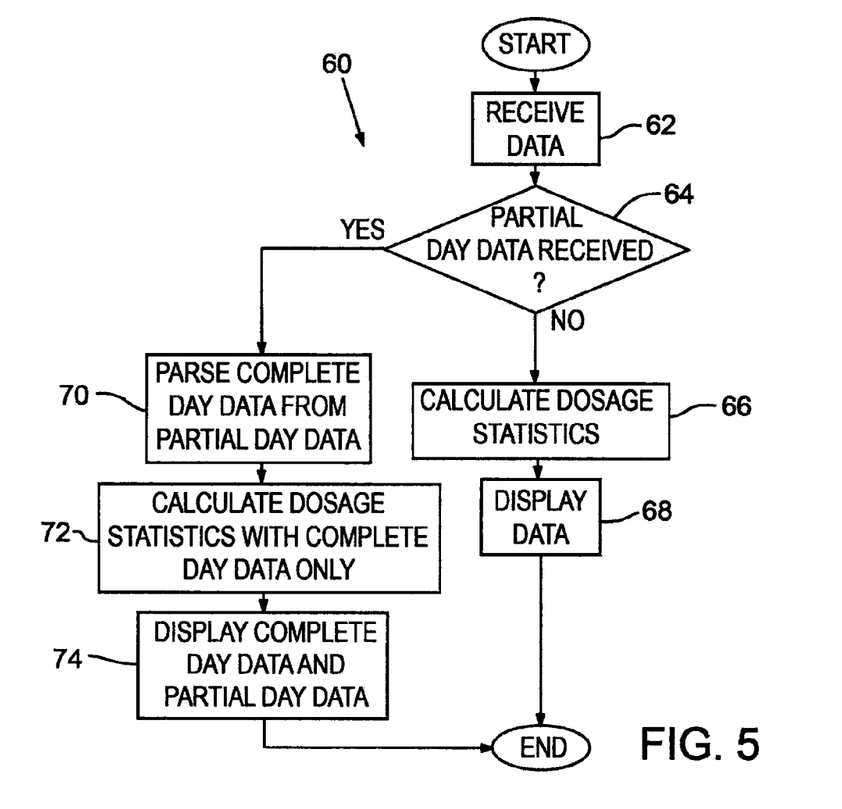
FIG. 5 is a flowchart representing exemplary methods of operating a data managing device of the system illustrated in FIG. 1.

FIG. 5 represents an exemplary method 60 of operating the data managing device 18 for processing and outputting the insulin dosage data transferred in block 54 of FIG. 4. As shown, the method 60 can begin in block 62, wherein the insulin dosage data 62 is received by the data managing device 18 (via the communication device 36 shown in FIG. 1). Then, in block 64, the processor 30 can determine whether any partial day dosage data is included in the data received in block 62. The processor 30 can rely on the end-of-day markers (described above and represented in column D of FIG. 2) for making this determination. For instance, the processor 30 can analyze the received data and if any data does not include an associated end-of-day marker, then it can be assumed that that particular data is "partial day dosage data" (i.e., block 64 answered affirmatively) and block 70 can follow. If all of the data received in block 62 includes associated end-of-day markers, then the processor 30 can determine that all of the data is "complete day dosage data" (i.e., block 64 answered negatively), and block 66 can follow.

In block 66, the processor 30 can utilize the data manager 31 software to calculate various dosage statistics using the data received in block 62. For instance, if only the complete day dosage data (lines 1-12 and 19-25 of FIG. 2) is received, then the processor 30 can calculate an average total units of insulin delivered per day, an average bolus units of insulin delivered per day, and/or an average basal units of insulin delivered per day. Then, in block 68 the data manager 31 can output the statistics in one or more ways. For instance, the data manager 31 can display the statistics textually and/or graphically (e.g., in a line graph) on the display 32. Also, the data manager 31 can send commands to a printer to output one or more hard copies of the statistics for use by physicians, the patient, etc.

In additional embodiments, block 64 can include a determination whether the data received in block 62 includes any basal data. If not (e.g., if the data only includes bolus data), then all the data can be used for calculating dosage statistics (block 66) and displayed (block 68). However, if the data received in block 62 includes basal data, then block 70 can follow.

Assuming that all of the data shown in FIG. 2 is transferred to the data managing device 18, then in block 64, the processor 30 can determine that there is both complete day dosage data and partial day dosage data included. Thus, in block 70, the data managing device 18 can parse the complete day dosage data (lines 1-12 and 19-25 of FIG. 2) from the partial day dosage data (lines 13-18 and 26).

In additional embodiments, the processor 22 of the pump 12 can continuously parse partial day data from the complete day data. Thus, when data is transferred to the data managing device 18, the received data is already parsed. As such, the processor 30 need not make the determination of block 64. Instead, block 62 can be followed directly by block 72. In still additional embodiments, the data managing device 18 can receive all data 62 and can then attempt to parse partial day data from complete day data even if there is no partial day data included. Stated differently, the data managing device 18 need not perform the determination of block 64.

Figure 3A:
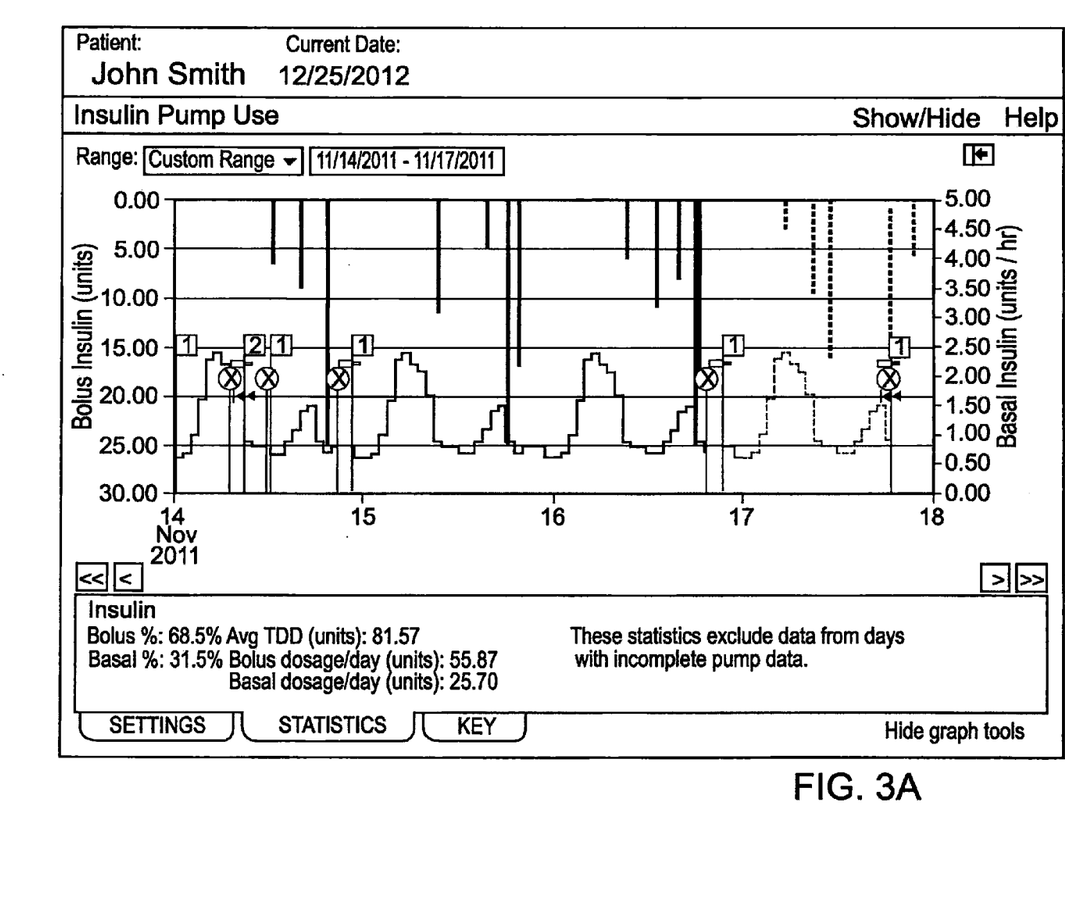
FIG. 3A is a graphic, specifically an exemplary line graph, displaying the insulin dosage data collected by the insulin management system of FIG. 1 and contained in the table of FIG. 2.

In block 72, the processor 30 can utilize the data manager 31 software to calculate dosage statistics using only the complete day dosage data (lines 1-12 and 19-25 of FIG. 2) and excluding the partial day dosage data (lines 13-18 and 26 of FIG. 2). As mentioned above, the statistics can include an average total units of insulin delivered per day, an average bolus units of insulin delivered per day, and/or an average basal units of insulin delivered per day. These statistics can be output for review by a physician, the patient, etc. For instance, the data manager 31 can send the statistics to be displayed on the display 32 of the data managing device 18 as represented at the bottom of FIG. 3A. Specifically, as shown in FIG. 3A, the respective percentages of bolus and basal dosages, the average units of insulin delivered per day, the units of bolus insulin delivered per day, and the units of basal insulin delivered per day can be displayed. Additionally, the display 32 can include a statement saying that the "statistics exclude data from days with incomplete pump data" to thereby inform the viewer that the statistics are not skewed due to inclusion of the partial day dosage data.

Accordingly, the data managing device 18 can automatically calculate the statistics for the convenience of the patient, the medical professional, etc. Also, since the partial day data is excluded from the calculations, the dosage calculations performed in block 72 can be very accurate.

Moreover, in block 74, the display 32 can display the dosage data and/or the statistics calculated in block 72. Also, in block 74, the display 32 can display both the complete day dosage data and the partial day dosage data. The data manager 31 can output the data and/or calculated statistics in other ways as well (e.g., by printing hard copies, by outputting the information audibly, etc.).

As shown in FIG. 3A, the display 32 can display the data included in FIG. 2 in a graphic, such as a line graph. (A key to the symbols included in FIG. 3A is included in FIG. 3B). It will be appreciated, however, that the data could be displayed as any other type of graphic (e.g., a pie chart, a scatter plot, tabular reports, etc.) and can include any appropriate symbols, colors, etc. without departing from the scope of the present disclosure.

As shown in the line graph of FIG. 3A, the display 32 can display the calendar date on the X-axis, the bolus insulin amount on the left-hand Y-axis, and the basal insulin flow rate on the right-hand Y-axis. Complete day bolus dosages (delivered November 14-16) can be displayed as solid, vertical bars that extend from the top of the graph. Partial day bolus dosages (delivered November 17) can be displayed as broken, vertical bars. Complete day basal dosages (delivered November 14-16) can be displayed as solid, stepped lines that extend horizontally across the graph, and partial day basal dosages (delivered November 17) can be displayed as broken, stepped lines. Accordingly, the complete day data (bolus and basal) can be quickly and clearly distinguished visually from the partial day data.

It will be appreciated that the display 32 can distinguish the complete day data from the partial day data in other ways as well. For instance, the lines representing the complete day data can have a different color from the lines representing the partial day data. Specifically, the display 32 can display complete day bolus dosages in a first color (e.g., red, etc.), the complete day basal dosages in a second color (e.g., blue, etc.), and the partial day bolus and basal dosages both in a third color (e.g., gray or other muted color). Moreover, in some embodiments, lines of different weights (thinner and thicker lines), different appearance (e.g., solid versus broken lines), etc. can be used to distinguish between the complete and partial day data. As such, the viewer can quickly and easily distinguish between the types of data.

In additional embodiments included in FIG. 3A, the display 32 can display additional information as well. For instance, during the measured time period (here, Nov. 14, 2011 to Nov. 17, 2011), the pump 12 can detect and record various events, such as a "shutdown event" of the insulin pump 12, and the display 32 can display the time that the shutdown event occurred. Specifically, if the reservoir 20 becomes empty, the battery 28 loses sufficient charge, or other condition arises in which the pump 12 is temporarily incapable of delivering insulin, then the processor 22 of the pump 12 can detect that the shutdown event has occurred, and the pump 12 can record the time of the shutdown event (e.g., the time of occurrence of the shutdown event, the duration of the shutdown event, etc.) into the memory device 24. The time of the shutdown event can be transferred to the data managing device 18 (e.g., with the data transferred in blocks 42 and 62), and the display 32 can include this information on the line graph with the dosage information. For instance, in the embodiments of FIG. 3A, times of several shutdown events are displayed with the letter "X" and a line extending downward to the X-axis.

Figure 3B:
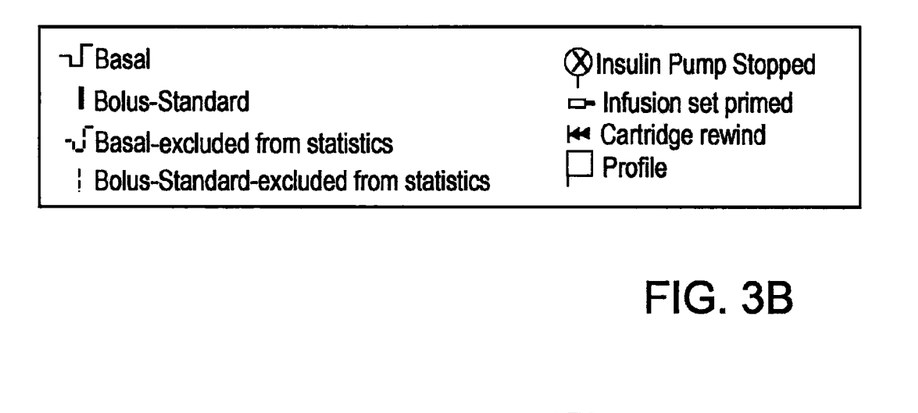
FIG. 3B is a key to the symbols included in the graphic of FIG. 3A.

The processor 22 can also detect other events. For instance, the processor 22 can detect an insulin refill event of the pump 12. Specifically, the processor 22 can detect rewind of the cartridge of the reservoir 20 (i.e., indicating a refill of the reservoir 20), and the processor 22 can detect the time that refill occurs (i.e., the refill time) from the clock 26. The processor 22 can also record the refill time into the memory device 24, and the refill time can be transferred to the data managing device 18. Then, the data manager 31 can use the display 32 for displaying the refill event and the corresponding refill time on the line graph as shown in FIG. 3A. In the embodiments of FIGS. 3A and 3B, the refill event is noted as two adjacent left-facing arrows.

Similarly, the processor 22 can be operable for detecting priming of the infusion set 14 for removing blockages therefrom (i.e., detecting a "priming event") and the time of occurrence of this event. The memory device 24 can record this information, and the communication device 29 can transfer this information to the data managing device 18. Then, the processor 30 can cause the display 32 to include this information on the line graph as shown in FIG. 3A. In the embodiments of FIGS. 3A and 3B, the priming event can be indicated as an icon resembling a screwdriver.

Those having ordinary skill in the art will understand that other events could also be detected and recorded by the pump 12. Corresponding data can then be transferred to the data managing device 18 for display on the display 32.

Additionally, as mentioned above, the processor 22 can control the amount, flow rate, and/or time of delivery based on one or more alternative programmed dosage profiles. In the embodiments of FIG. 2, there is a first basal dosage profile (indicated by the number "1") and a second basal dosage profile (indicated by the number "2"). In the illustrated embodiments, the basal insulin is delivered according to the first basal dosage profile in all but the time period of 8:54 AM to 11:58 AM on Nov. 14, 2011 (column C, line 20). The processor 22 can automatically change the profile according to programmed logic, or the user can manually input commands for changing the profile. Regardless, the insulin pump 12 can record "profile data" that indicates whether the basal dosages are delivered according to the first profile or the second profile. The pump 12 can transfer this "profile data" to the data managing device 18 in blocks 54 (FIG. 4) and block 62 (FIG. 5), and the display 32 can display the "profile data." For instance, as shown in FIG. 3A, the line graph can include flags with either the number "1" or the number "2" to indicate which profile was governing the basal dosages. The lines following the flags representing the different basal dosages can also be graphically different (e.g., the basal dosage lines following the "1" flags can be displayed in one color while the basal dosage line following the "2" flag can be displayed in a different color).

Accordingly, the dosage data and the calculated statistics can be presented and summarized in a convenient and useful manner for the patient, a medical professional, etc. Also, using the displayed data and/or the statistics, future dosages can be planned, treatment can be altered, etc. Also, because the partial day dosage data is automatically recognized and excluded from the statistical calculations, the statistics can be an accurate reflection of the delivery of insulin.

As a simplified example of why the statistics would be more accurate, consider a pump 12 that delivers dosages at a steady rate for a total of ten units of insulin per day. Also, the pump 12 delivers the insulin according to this schedule for three complete days and for twelve hours on the fourth day. Data is transferred to the data managing device 18 at the end of the twelfth hour on the fourth day. The methods disclosed herein (i.e., excluding the twelve hours on the fourth day from the statistical calculation) would accurately show that the average daily dosage was ten units per day (i.e., 30 units/3 days=10 units/day). However, if the partial day data were included in the statistical calculation, then the calculated average daily dosage would be 8.75 units per day (i.e., 35 units/4 days=8.75 units/day).

Moreover, as shown in FIG. 3A, the display 32 of the data managing device 18 can display the data and statistics in a manner that allows the user to customize what is displayed and/or allows the user to interact with the displayed information. For instance, as shown in FIG. 3A, the time period can be selectively adjusted using pull-down menus and/or data entry boxes. (An exemplary pull-down menu labeled "Custom Range" is shown in FIG. 3A, and an exemplary data entry box is labeled "Nov. 14, 2011-Nov. 17, 2011"). Thus, the user can select which time period should be used for performing the calculations and/or for displaying dosage data. Moreover, as indicated by the "<<" and "<" symbols in FIG. 3A, the display 32 can allow the user to scroll to data collected at an earlier date, and as indicated by the ">>" and ">" symbols, the display 32 can allow the user to scroll to data collected at later dates.

In some embodiments, the pump 12 collects the dosage data in a continuous manner until the pump 12 receives a command to transfer the collection of data to the data managing device 18. It will be appreciated that the pump 12 can receive the transfer command before the completion of the respective day; therefore, the pump 12 will transfer partial day data for the day the command is received by the pump 12. (In the embodiments of FIG. 2, the pump 12 receives the command at 9:38 PM on Nov. 17, 2011, making the dosages of Nov. 17, 2011 partial day data). However, the pump 12 can continue to record dosage data for the remainder of that day (i.e., the pump 12 can record "remainder data") even after the transfer command is received. In this case, the processor 22 can associate the remainder data with the previously recorded partial day data. Then, upon completion of the day (e.g., 11:59 PM and 59 seconds on Nov. 17, 2011), the processor 22 can detect the end-of-day event and associate the end-of-day marker with the data for that entire day. Next, the data and associated end-of-day marker can be transferred to the data managing device 18, which will now consider that day's data as complete day data. Thus, the data for that day can be included in the calculations of the average daily dosage, etc. as described above. Moreover, the data for that day can be displayed with the other complete day data.

In additional embodiments, data on the pump 12 might include only partial day data. When transferred to the data managing device 18, the processor 30 can determine that only partial day data is included. As a result, the processor 30 can display the partial day data graphically according to the above discussion. Also, in some embodiments, the processor 30 can prevent daily dosage averages or other statistics to be calculated using this partial day data.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

What is claimed is:

1. A computer-implemented method for managing insulin dosage data collected over the course of multiple days to a person having diabetes, comprising:
   providing, by an insulin pump, a plurality of insulin dosages over a time period;
   recording, by the insulin pump into a memory device, the plurality of insulin dosages;
   recognizing, by the insulin pump, a completion of a subject day, wherein the multiple days include the subject day;

recording, by the insulin pump into the memory device, an end-of-day marker as a result of recognizing the completion of the subject day;

associating, by the insulin pump, the end-of-day marker to those of the plurality of insulin dosages delivered during the subject day;

receiving, by a data managing device from the insulin pump, the plurality of insulin dosages and the end-of-day marker associated with those of the plurality of insulin dosages delivered during the subject day;

identifying, by the data managing device, those of the plurality of insulin dosages associated with the end-of-day marker as complete day dosage data;

identifying, by the data managing device, those of the plurality of insulin dosages unassociated with the end-of-day marker as partial day dosage data;

performing, by the data managing device, a calculation of insulin dosage statistics, the calculation including the complete day dosage data, the calculation excluding the partial day dosage data; and displaying, by the data managing device, both the complete day dosage data and the partial day dosage data to distinguish between the complete day dosage data and the partial day dosage data.

2. The method of claim 1, wherein the plurality of insulin dosages includes a plurality of basal insulin dosages and a plurality of bolus insulin dosages.

3. The method of claim 1, wherein the insulin dosage statistics includes at least one of an average total units of insulin delivered per day, an average bolus units of insulin delivered per day, and an average basal units of insulin delivered per day.

4. The method of claim 1, wherein displaying both the complete day dosage data and the partial day dosage data includes distinguishing between the complete day dosage data and the partial day dosage data by displaying the complete day dosage data with a different color from the partial day dosage data.

5. The method of claim 1, wherein displaying both the complete day dosage data and the partial day dosage data includes displaying a single graphic showing both the complete dosage data and the partial day dosage data.

6. The method of claim 5, wherein the complete day dosage data includes a complete day basal dosage data and a complete day bolus dosage data, wherein the partial day dosage data includes a partial day basal dosage data and a partial day bolus dosage data, wherein the complete day basal dosage data is displayed in a first color, the complete day bolus dosage data is displayed in a second color, wherein both the partial day basal dosage data and the partial day bolus dosage data are displayed in a third color, and wherein the first, second, and third colors are different from each other.

7. The method of claim 5, further comprising:
recording, by the insulin pump into the memory device, a shutdown event of the insulin pump, the shutdown event being a lack of capability of the insulin pump to deliver insulin;
transferring the shutdown event from the insulin pump to the data managing device; and
displaying, by the data managing device, the shutdown event on the graphic.

8. The method of claim 7, further comprising:
recording, by the insulin pump into the memory device, an insulin refill event of the insulin pump;
transferring the refill event from the insulin pump to the data managing device; and
displaying, by the data managing device, the refill event on the graphic.

9. The method of claim 5, wherein the insulin pump is operable to pump insulin according to a first predetermined profile and, alternatively, according to a second predetermined profile, the method further comprising:
recording, by the insulin pump into the memory device, profile data, the profile data indicating which of the plurality of insulin dosages are delivered according to the first predetermined profile and which of the plurality of insulin dosages are delivered according to the second predetermined profile;
transferring the profile data from the insulin pump to the data managing device; and
displaying, by the data managing device, the profile data on the graphic.

10. The method of claim 5, wherein the graphic is a line graph with a first line indicating the complete dosage data and a second line indicating the partial day dosage data.

11. The method of claim 1, further comprising transferring the plurality of insulin dosages and the end-of-day marker associated with those of the plurality of insulin dosages delivered during the complete day from the insulin pump to the data managing device.

12. An insulin management system that manages insulin dosage data collected over the course of multiple days to a person having diabetes, the insulin management system comprising:
an insulin pump with a memory device, the insulin pump being operable to provide a plurality of insulin dosages over a time period, the time period including a complete day and a partial day, the insulin pump operable to record the plurality of insulin dosages into the memory device, the insulin pump operable to recognize a completion of the complete day and record an end-of-day marker into the memory device as a result of the completion of the complete day, the insulin pump further operable to associate the end-of-day marker to those of the plurality of insulin dosages delivered during the complete day; and
a data managing device that is operable to receive from the insulin pump the plurality of insulin dosages and the end-of-day marker associated with those of the plurality of insulin dosages delivered during the complete day, the data managing device operable to identify those of the plurality of insulin dosages associated with the end-of-day marker as complete day dosage data, the data managing device also operable to identify those of the plurality of insulin dosages unassociated with the end-of-day marker as partial day dosage data, the data managing device further including at least one of:
a processor that is operable to perform a calculation of insulin dosage statistics, the calculation including the complete day dosage data, the calculation excluding the partial day dosage data, and
a display that is operable to display both the complete day dosage data and the partial day dosage data to distinguish between the complete day dosage data and the partial day dosage data.

13. The insulin management system of claim 12, wherein the plurality of insulin dosages includes a plurality of basal insulin dosages and a plurality of bolus insulin dosages.

14. The insulin management system of claim 12, wherein the insulin dosage statistics includes at least one of an average total units of insulin delivered per day, an average bolus units of insulin delivered per day, and an average basal units of insulin delivered per day.

15. The insulin management system of claim 12, wherein the display is operable to distinguish between the complete day dosage data and the partial day dosage data by displaying the complete day dosage data with a different color from the partial day dosage data.

16. The insulin management system of claim 12, wherein the display is operable to display a single graphic showing both the complete dosage data and the partial day dosage data.

17. The insulin management system of claim 16, wherein the complete day dosage data includes a complete day basal dosage data and a complete day bolus dosage data, wherein the partial day dosage data includes a partial day basal dosage data and a partial day bolus dosage data, wherein the display is operable to display the complete day basal dosage data in a first color, wherein the display is operable to display the complete day bolus dosage data in a second color, and wherein the display is operable to display both the partial day basal dosage data and the partial day bolus dosage data in a third color, and wherein the first, second, and third colors are different from each other.

18. The insulin management system of claim 16, wherein the insulin pump is operable to record into the memory device a shutdown event of insulin delivery by the insulin pump, the shutdown event being a lack of capability of the insulin pump to deliver insulin, wherein the insulin pump is operable to transfer the shutdown event to the data managing device, and wherein the display is operable to display the shutdown event on the graphic.

19. The insulin management system of claim 18, wherein the insulin pump is operable to record into the memory device an insulin refill event of the insulin pump, wherein the insulin pump is operable to transfer the refill event to the data managing device, and wherein the display is operable to display the refill event on the graphic.

20. The insulin management system of claim 16, wherein the insulin pump is operable to pump insulin according to a first predetermined profile and, alternatively, according to a second predetermined profile, wherein the insulin pump is operable to record into the memory device profile data, the profile data indicating which of the plurality of dosages are delivered according to the first predetermined profile and which of the plurality of insulin dosages are delivered according to the second predetermined profile, wherein the insulin pump is operable to transfer the profile data to the data managing device, and wherein the data managing device is operable to display the profile data on the graphic.

21. A computer-implemented method for managing insulin dosage data collected by an insulin pump over the course of multiple days to a person having diabetes comprising:
receiving, by a data managing device from an insulin pump, a collection of data that reflects a plurality of insulin dosages delivered by the insulin pump over the course of a complete day and a partial day, the collection of data also including an end-of-day marker that the insulin pump has associated with those of the plurality of insulin dosages delivered throughout the complete day;
identifying, by the data managing device, those of the plurality of insulin dosages associated with the end-of-day marker as complete day dosage data;
identifying, by the data managing device, those of the plurality of insulin dosages unassociated with the end-of-day marker as partial day dosage data; and
at least one of:
performing, by the data managing device, a calculation of insulin dosage statistics, the calculation including the complete day dosage data, the calculation excluding the partial day dosage data; and
displaying, by the data managing device, both the complete day dosage data and the partial day dosage data to distinguish between the complete day dosage data and the partial day dosage data.

22. A computer-implemented method for managing insulin dosage data administered over the course of multiple days to a person having diabetes, comprising:
providing, by an insulin pump, a plurality of insulin dosages over a time period, the plurality of insulin dosages including a plurality of basal insulin dosages and a plurality of bolus insulin dosages;
recording, by the insulin pump into a memory device, the plurality of insulin dosages;
recognizing, by the insulin pump, a completion of a subject day wherein the multiple days include the subject day;
recording, by the insulin pump into the memory device, an end-of-day marker as a result of recognizing the completion of the subject day;
associating, by the insulin pump, the end-of-day marker to those of the plurality of insulin dosages delivered during the subject day;
transferring the plurality of insulin dosages and the end-of-day marker associated with those of the plurality of insulin dosages delivered during the subject day from the insulin pump to a data managing device;
identifying, by the data managing device, those of the plurality of insulin dosages associated with the end-of-day marker as complete day dosage data;
identifying, by the data managing device, those of the plurality of insulin dosages unassociated with the end-of-day marker as partial day dosage data;
performing, by the data managing device, a calculation of insulin dosage statistics, the calculation including the complete day dosage data, the calculation excluding the partial day dosage data; and
displaying, by the data managing device, both the complete day dosage data and the partial day dosage data to distinguish between the complete day dosage data and the partial day dosage data.

* * * * *